United States Patent
Orme et al.

(10) Patent No.: US 6,911,542 B2
(45) Date of Patent: Jun. 28, 2005

(54) PYRAZINO[1',2':1,6]PYRIDO[3,4B]INDOLE DERIVATIVES

(75) Inventors: Mark W. Orme, Seattle, WA (US); Jason Scott Sawyer, Indianapolis, IN (US); Lisa M. Schultze, Woodinville, WA (US); Alain Claude-Marie Daugan, Les Ulis (FR); Francoise Gellibert, Les Ulis (FR)

(73) Assignee: Lilly Icos LLC., Wilmington, DE (US)

( * ) Notice: Subject to any disclaimer, the term of this patent is extended or adjusted under 35 U.S.C. 154(b) by 0 days.

(21) Appl. No.: 10/297,682

(22) PCT Filed: May 15, 2001

(86) PCT No.: PCT/US01/15935

§ 371 (c)(1),
(2), (4) Date: Dec. 6, 2002

(87) PCT Pub. No.: WO02/00656

PCT Pub. Date: Jan. 3, 2002

(65) Prior Publication Data

US 2003/0225094 A1 Dec. 4, 2003

Related U.S. Application Data

(60) Provisional application No. 60/213,647, filed on Jun. 23, 2000.
(51) Int. Cl.$^7$ ............................................. C07D 471/14
(52) U.S. Cl. ..................................................... 544/343
(58) Field of Search ........................... 514/214.03, 250, 514/233.2; 540/585; 544/343, 115

(56) References Cited

FOREIGN PATENT DOCUMENTS

WO    WO 95/19978    7/1995

OTHER PUBLICATIONS

Perry, M.J. et al, Current Opinion in Chemical Biology, 1998, 2, 472–481.*

Corbin JD, Francis SH., Int J Clin Pract. Jul.–Aug. 2002;56(6):453–9.*

Cremers B, Bohm M., Herz. Jun. 2003;28(4):325–333.*

* cited by examiner

*Primary Examiner*—Thomas C. McKenzie
(74) *Attorney, Agent, or Firm*—Marshall, Gerstein & Borun LLP

(57) ABSTRACT

Compounds of the general structural formula (I) and use of the compounds and salts and solvates thereof, as therapeutic agents.

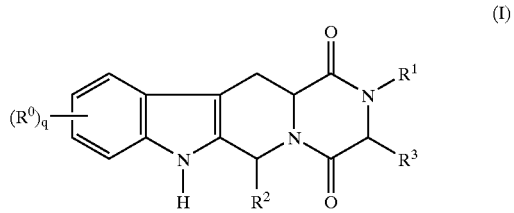

(I)

1 Claim, No Drawings

PYRAZINO[1',2':1,6]PYRIDO[3,4B]INDOLE DERIVATIVES

CROSS REFERENCE TO RELATED APPLICATION

This is the U.S. national phase application of International Application No. PCT/US01/15935, filed May 15, 2001, which claims the benefit of U.S. provisional patent application Ser. No. 60/213,647, filed Jun. 23, 2000.

FIELD AND BACKGROUND OF THE INVENTION

This invention relates to a series of compounds, to methods of preparing the compounds, to pharmaceutical compositions containing the compounds, and to their use as therapeutic agents. In particular, the invention relates to compounds that are potent and selective inhibitors of cyclic guanosine 3', 5'-monophosphate specific phosphodiesterase (cGMP-specific PDE), in particular PDE5, and have utility in a variety of therapeutic areas wherein such inhibition is considered beneficial, including the treatment of cardiovascular disorders and erectile dysfunction.

SUMMARY OF THE INVENTION

The present invention provides compounds of formula (I)

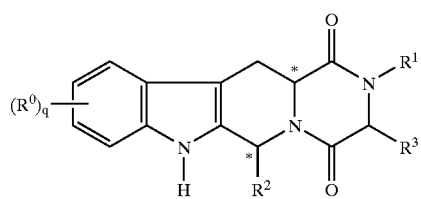

(I)

wherein $R^0$, independently, is selected from the group consisting of halogen and $C_{1-6}$alkyl;

$R^1$ is selected from the group consisting of aryl, heteroaryl, $OR^a$, $SR^a$, $NR^aR^b$, $NR^aR^c$, $NR^aC(=O)R^b$, $NR^aC(=O)R^c$, $C(=O)R^a$, $C(=O)OR^a$, $C(=O)NR^aR^b$, $C(=O)NR^aR^c$, $C(=O)SR^a$, $C(=S)NR^aR^b$, $C(=S)NR^aR^c$, $SO_2R^a$, $SO_2NR^aR^b$, $SO_2NR^aR^c$, $S(=O)R^a$, $S(=O)NR^aR^b$, $S(=O)NR^aR^c$, $PO_3R^a$, CN, $C(=O)NR^aC_{1-4}$alkyleneOR$^a$, $C(=O)NR^aC_{1-4}$alkyleneHet, $C(=O)$-$C_{1-4}$alkylenearyl, $C(=O)C_{1-4}$alkyleneheteroaryl, $C_{1-4}$-alkylenearyl substituted with one or more of $SO_2NR^aR^b$, $NR^aR^b$, $C(=O)OR^a$, $NR^aSO_2CF_3$, CN, $NO_2$, $C(=O)R^a$, $OR^a$, $C_{1-4}$alkyleneNR$^aR^b$, and $OC_{1-4}$alkyleneNR$^aR^b$, $C_{1-4}$alkyleneheteroaryl (with the proviso that heteroaryl is different from thienyl, furyl, and pyridyl), $C_{1-4}$-alkyleneHet, $C_{1-4}$alkyleneC(=O)C$_{1-4}$alkylenearyl, $C_{1-4}$-alkyleneC(=O)C$_{1-4}$alkyleneheteroaryl, $C_{1-4}$alkyleneC(=O)Het, $C_{1-4}$alkyleneC(=O)NR$^aR^b$, $C_{1-4}$alkyleneC(=O)-NR$^aR^c$, $C_{1-4}$alkyleneOR$^a$, $C_{1-4}$alkyleneNR$^aC(=O)R^a$, $C_{1-4}$-alkyleneOC$_{1-4}$alkyleneOR$^a$, $C_{1-4}$alkyleneNR$^aR^b$, $C_{1-4}$alkyleneNR$^aR^c$, $C_{1-4}$alkyleneC(=O)OR$^a$, and $C_{1-4}$alkyleneOC$_{1-4}$-alkyleneC(=O)OR$^a$;

$R^2$ is selected from the group consisting of an optionally substituted monocyclic aromatic ring selected from the group consisting of benzene, thiophene, furan, and pyridine, and an optionally substituted bicyclic ring

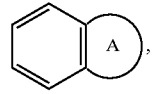

wherein the fused ring A is a 5- or 6-membered ring, saturated or partially or fully unsaturated, and comprises carbon atoms and optionally one or two heteroatoms selected from oxygen, sulfur, and nitrogen;

$R^3$ is selected from the group consisting of hydrogen and $C_{1-6}$alkyl;

$R^a$ and $R^b$, independently, are selected from the group consisting of hydrogen, $C_{1-6}$alkyl, $C_{3-8}$cycloalkyl, aryl, heteroaryl, aryl$C_{1-3}$alkyl, heteroaryl-$C_{1-3}$alkyl, $C_{1-3}$alkylenearyl, $C_{1-3}$alkyleneheteroaryl, and Het;

$R^c$ is phenyl or $C_{4-6}$cycloalkyl, either optionally substituted with one or more substituent selected from the group consisting of halo, $C(=O)OR^a$, and $OR^a$;

Het represents a heterocyclic group, saturated or partially unsaturated, containing at least one heteroatom selected from the group consisting of oxygen, nitrogen, and sulfur, and optionally substituted with $C_{1-4}$alkyl or $C(=O)OR^b$;

q is 1, 2, 3, or 4; and pharmaceutically acceptable salts and hydrates thereof.

As used herein, the term "alkyl" includes straight chained and branched hydrocarbon groups containing the indicated number of carbon atoms, typically methyl, ethyl, and straight chain and branched propyl and butyl groups. The hydrocarbon group can contain up to 16 carbon atoms. The term "alkyl" includes "bridged alkyl," i.e., a $C_6$–$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. The term "cycloalkyl" is defined as a cyclic $C_3$–$C_8$ hydrocarbon group, e.g., cyclopropyl, cyclobutyl, cyclohexyl, and cyclopentyl.

The terms "alkenyl" and "alkynyl" are defined identically as "alkyl," except for containing a carbon-carbon double bond or carbon-carbon triple bond, respectively.

The term "alkylene" refers to an alkyl group having a substituent. For example, the term "$C_{1-3}$alkylenearyl" refers to an alkyl group containing one to three carbon atoms, and substituted with an aryl group. The term "alkenylene" as used herein is similarly defined, and contains the indicated number of carbon atoms and a carbon-carbon double bond, and includes straight chained and branched alkenylene groups, like ethyenylene.

The term "halo" or "halogen" is defined herein to include fluorine, bromine, chlorine, and iodine.

The term "haloalkyl" is defined herein as an alkyl group substituted with one or more halo substituents, either fluoro, chloro, bromo, iodo, or combinations thereof. Similarly, "halocycloalkyl" is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to three, halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of aryl groups include, but are not limited to, phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like.

The term "Het" is defined as saturated or partially unsaturated monocyclic, bicyclic, and tricyclic groups containing one or more heteroatoms selected from the group consisting of oxygen, nitrogen, and sulfur. A "Het" group also can contain an oxo group (=O) attached to the ring. Nonlimiting examples of Het groups include 1,3-dioxolane, 2-pyrazoline, pyrazolidine, pyrrolidine, a pyrroline, 2H-pyran, 4H-pyran, morpholine, thiomorpholine, piperidine, 1,4-dithiane, and 1,4-dioxane.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include, but are not limited to, thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "hydroxy" is defined as —OH.

The term "alkoxy" is defined as —OR, wherein R is alkyl.

The term "alkoxyalkyl" is defined as an alkyl group wherein a hydrogen has been replaced by an alkoxy group. The term "(alkylthio)alkyl" is defined similarly as alkoxyalkyl, except a sulfur atom, rather than an oxygen atom, is present.

The term "hydroxyalkyl" is defined as a hydroxy group appended to an alkyl group.

The term "amino" is defined as —$NH_2$, and the term "alkylamino" is defined as —$NR_2$, wherein at least one R is alkyl and the second R is alkyl or hydrogen.

The term "acylamino" is defined as RC(=O)N, wherein R is alkyl or aryl.

The term "alkylthio" is defined as —SR, wherein R is alkyl.

The term "alkylsulfinyl" is defined as R—$SO_2$, wherein R is alkyl.

The term "alkylsulfonyl" is defined as R—$SO_3$, wherein R is alkyl.

The term "nitro" is defined as —$NO_2$.

The term "trifluoromethyl" is defined as —$CF_3$.

The term "trifluoromethoxy" is defined as —$OCF_3$.

The term "cyano" is defined as —CN.

In preferred embodiments, $R^1$ is selected from the group consisting of aryl, heteroaryl, $OR^a$, $NR^aR^b$, $NR^aR^c$, $C_{1-4}$alkyleneHet, $C_{1-4}$alkyleneheteroaryl, $C_{1-4}$alkylenearyl, $C_{1-4}$alkyleneC(=O)$C_{1-4}$alkylenearyl, $C_{1-4}$alkyleneC(=O)$OR^a$, $C_{1-4}$alkyleneC(=O)$NR^aR^b$, $C_{1-4}$alkyleneC(=O)$NR^aR^c$, $C_{1-4}$alkyleneC(=O)Het, $C_{1-4}$alkyleneNR$^aR^b$, $C_{1-4}$alkyleneNR$^aR^c$, $C_{1-4}$alkyleneNR$^a$C(=O)$R^a$, and $C_{1-4}$-alkyleneOC$_{1-4}$alkyleneOR$^a$.

In more preferred embodiments, $R^1$ is selected from the group consisting of $C_{1-4}$alkyleneheteroaryl, wherein the heteroaryl group is selected from the group consisting of benzimidazole, a triazole, and imidazole; $C_{1-4}$alkyleneHet, wherein Het is selected from the group consisting of piperazine, morpholine, pyrrolidine, pyrrolidone, tetrahydrofuran, piperidine,

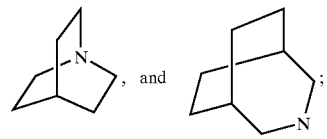

$C_{1-4}$alkyleneC$_6$H$_5$, optionally substituted with one to three groups selected from the group consisting of C(=O)OR$^a$, NR$^aR^b$, NR$^a$SO$_2$CF$_3$, SO$_2$NR$^aR^b$, CN, OR$^a$, C(=O)R$^a$, $C_{1-4}$alkyleneNR$^aR^b$, nitro, OC$_{1-4}$alkylenearyl, and OC$_{1-4}$alkyleneNR$^aR^b$; $C_{1-4}$alkyleneC(=O)benzyl; $C_{1-4}$alkyleneC(=O)OR$^a$; $C_{1-4}$alkyleneC(=O)NR$^aR^b$; $C_{1-4}$alkyleneC(=O)—NR$^aR^c$; $C_{1-4}$alkyleneHet; NR$^aR^b$; OH; OC$_{1-4}$alkyl; C$_6$H$_5$; $C_{1-4}$alkyleneNR$^aR^b$; $C_{1-4}$alkyleneOR$^a$; $C_{1-4}$alkyleneNHC(=O)R$^a$; and $C_{1-4}$alkyleneOC$_{1-4}$alkyleneOR$^a$.

In a preferred embodiment, $R^2$ is the optionally substituted bicyclic ring system

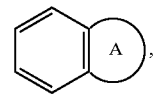

wherein the bicyclic ring can represent, for example, naphthalene or indene, or a heterocycle, such as benzoxazole, benzothiazole, benzisoxazole, benzimidazole, quinoline, indole, benzothiophene, or benzofuran, or

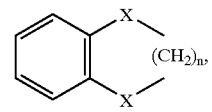

wherein n is an integer 1 or 2, and X, independently, are C(R$^a$)$_2$, O, S, or NR$^a$. The bicyclic ring comprising the $R^2$ substituent typically is attached to the rest of the molecule by a phenyl ring carbon atom.

In a preferred group of compounds of formula (I), $R^2$ is represented by methoxyphenyl or an optionally substituted bicyclic ring

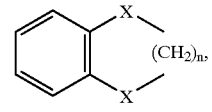

wherein n is 1 or 2, and X, independently, are CH$_2$ or O. Especially preferred $R^2$ substituents include

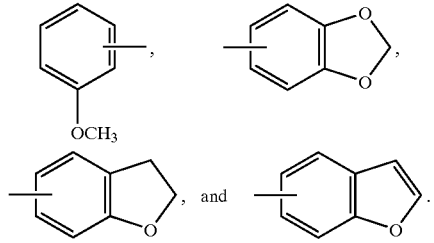

Within this particular group of compounds, nonlimiting examples of substituents for the $R^2$ substituent include halogen (e.g., chlorine), $C_{1-3}$alkyl (e.g., methyl, ethyl, or i-propyl), OR$^a$ (e.g., methoxy, ethoxy, or hydroxy), CO$_2$R$^a$, halomethyl or halomethoxy (e.g., trifluoromethyl or trifluoromethoxy), cyano, nitro, and $NR^aR^b$.

An especially preferred subclass of compounds within the general scope of formula (I) is represented by compounds of formula (II)

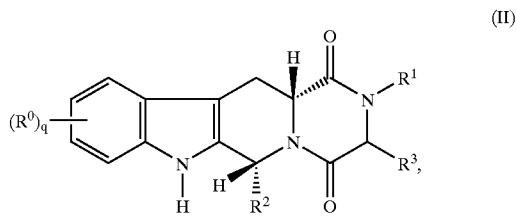

(II)

and pharmaceutically acceptable salts and solvates (e.g., hydrates) thereof.

Compounds of formula (I) can contain one or more asymmetric center, and, therefore, can exist as stereoisomers. The present invention includes both mixtures and separate individual stereoisomers of the compounds of formula (I). Compounds of formula (I) also can exist in tautomeric forms, and the invention includes both mixtures and separate individual tautomers thereof.

Pharmaceutically acceptable salts of the compounds of formula (I) can be acid addition salts formed with pharmaceutically acceptable acids. Examples of suitable salts include, but are not limited to, the hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, and p-toluenesulfonate salts. The compounds of the formula (I) also can provide pharmaceutically acceptable metal salts, in particular alkali metal salts and alkaline earth metal salts, with bases. Examples include the sodium, potassium, magnesium, and calcium salts.

Compounds of the present invention are potent and selective inhibitors of cGMP-specific PDE5. Thus, compounds of formula (I) are of interest for use in therapy, specifically for the treatment of a variety of conditions where selective inhibition of PDE5 is considered beneficial.

Phosphodiesterases (PDEs) catalyze the hydrolysis of cyclic nucleotides, such as cyclic adenosine monophosphate (cAMP) and cyclic guanosine monophosphate (cGMP). The PDEs have been classified into at least seven isoenzyme families and are present in many tissues (J. A. Beavo, *Physiol. Rev.*, 75, p. 725 (1995)).

PDE5 inhibition is a particularly attractive target. A potent and selective inhibitor of PDE5 provides vasodilating, relaxing, and diuretic effects, all of which are beneficial in the treatment of various disease states. Research in this area has led to several classes of inhibitors based on the cGMP basic structure (E. Sybertz et al., *Expert. Opin. Ther. Pat.*, 7, p. 631 (1997)).

The biochemical, physiological, and clinical effects of PDE5 inhibitors therefore suggest their utility in a variety of disease states in which modulation of smooth muscle, renal, hemostatic, inflammatory, and/or endocrine function is desirable. The compounds of formula (I), therefore, have utility in the treatment of a number of disorders, including stable, unstable, and variant (Prinzmetal) angina, hypertension, pulmonary hypertension, chronic obstructive pulmonary disease, malignant hypertension, pheochromocytoma, congestive heart failure, acute respiratory distress syndrome, acute and chronic renal failure, atherosclerosis, conditions of reduced blood vessel patency (e.g., postpercutaneous transluminal coronary or carotid angioplasty, or post-bypass surgery graft stenosis), peripheral vascular disease, vascular disorders, such as Raynaud's disease, thrombocythemia, inflammatory diseases, myocardial infarction, stroke, bronchitis, chronic asthma, allergic asthma, allergic rhinitis, glaucoma, osteoporosis, preterm labor, benign prostatic hypertrophy, peptic ulcer, preterm labor, benign prostatic hypertrophy, male erectile dysfunction, female sexual dysfunction, and diseases characterized by disorders of gut motility (e.g., irritable bowel syndrome).

An especially important use is the treatment of male erectile dysfunction, which is one form of impotence and is a common medical problem. Impotence can be defined as a lack of power, in the male, to copulate, and can involve an inability to achieve penile erection or ejaculation, or both. The incidence of erectile dysfunction increases with age, with about 50% of men over the age of 40 suffering from some degree of erectile dysfunction.

In addition, a further important use is the treatment of female arousal disorder, also termed female sexual arousal disorder. Female arousal disorders are defined as a recurrent inability to attain or maintain an adequate lubrication/swelling response of sexual excitement until completion of sexual activity. The arousal response consists of vasocongestion in the pelvis, vaginal lubrication, and expansion and swelling of external genitalia.

It is envisioned, therefore, that compounds of formula (I) are useful in the treatment of male erectile dysfunction and female sexual arousal disorder. Thus, the present invention concerns the use of compounds of formula (I), or a pharmaceutically acceptable salt thereof, or a pharmaceutical composition containing either entity, for the manufacture of a medicament for the curative or prophylactic treatment of erectile dysfunction in a male animal and sexual arousal disorder in a female animal, including humans.

The term "treatment" includes preventing, lowering, stopping, or reversing the progression or severity of the condition or symptoms being treated. As such, the term "treatment" includes both medical therapeutic and/or prophylactic administration, as appropriate.

It also is understood that "a compound of formula (I)," or a physiologically acceptable salt or solvate thereof, can be administered as the neat compound, or as a pharmaceutical composition containing either entity.

Although the compounds of the invention are envisioned primarily for the treatment of sexual dysfunction in humans, such as male erectile dysfunction and female sexual arousal disorder, they also can be used for the treatment of other disease states.

A further aspect of the present invention, therefore, is providing a compound of formula (I) for use in the treatment of stable, unstable, and variant (Prinzmetal) angina, hypertension, pulmonary hypertension, chronic obstructive pulmonary disease, malignant hypertension, pheochromocytoma, congestive heart failure, acute respiratory distress syndrome, acute and chronic renal failure, atherosclerosis, conditions of reduced blood vessel patency (e.g., post-PTCA or post-bypass graft stenosis), peripheral vascular disease, vascular disorders such as Raynaud's disease, thrombocythemia, inflammatory diseases, prophylaxis of myocardial infarction, prophylaxis of stroke, stroke, bronchitis, chronic asthma, allergic asthma, allergic rhinitis, glaucoma, osteoporosis, preterm labor, benign prostatic hypertrophy, male and female erectile dysfunction, or diseases characterized by disorders of gut motility (e.g., IBS).

According to another aspect of the present invention, there is provided the use of a compound of formula (I) for the manufacture of a medicament for the treatment of the above-noted conditions and disorders.

In a further aspect, the present invention provides a method of treating the above-noted conditions and disorders in a human or nonhuman animal body which comprises administering to said body a therapeutically effective amount of a compound of formula (I).

Compounds of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

Oral administration of a compound of the invention is the preferred route. Oral administration is the most convenient and avoids the disadvantages associated with other routes of administration. For patients suffering from a swallowing disorder or from impairment of drug absorption after oral administration, the drug can be administered parenterally, e.g., sublingually or buccally.

Compounds and pharmaceutical compositions suitable for use in the present invention include those wherein the active ingredient is administered in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a range of dosage for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

The amount of composition administered is dependent on the subject being treated, on the subject's weight, the severity of the affliction, the manner of administration, and the judgment of the prescribing physician.

Specifically, for administration to a human in the curative or prophylactic treatment of the conditions and disorders identified above, oral dosages of a compound of formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

For human use, a compound of the formula (I) can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of formula (I) into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a compound of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% compound of the present invention, and preferably from about 25% to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5% to about 90% by weight of a compound of the present invention, and preferably about 1% to about 50% of a compound of the present invention.

When a therapeutically effective amount of a compound of the present invention is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

For oral administration, the compounds can be formulated readily by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Many of the compounds of the present invention can be provided as salts with pharmaceutically compatible counterions. Such pharmaceutically acceptable base addition salts are those salts that retain the biological effectiveness and properties of the free acids, and that are obtained by reaction with suitable inorganic or organic bases.

In particular, a compound of formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound preferably is used in the form of a sterile aqueous solution which can contain other substances, for example, salts, or monosaccharides, such as mannitol or glucose, to make the solution isotonic with blood.

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor. There is further provided by the present invention a process of preparing a pharmaceutical composition comprising a compound of formula (I), which process comprises mixing a compound of formula (I), together with a pharmaceutically acceptable diluent or carrier therefor.

In a particular embodiment, the invention includes a pharmaceutical composition for the curative or prophylactic treatment of erectile dysfunction in a male animal, or sexual arousal disorder in a female animal, including humans, comprising a compound of formula (I) or a pharmaceutically acceptable salt thereof, together with a pharmaceutically acceptable diluent or carrier.

Compounds of formula (I) can be prepared by any suitable method known in the art, or by the following processes which form part of the present invention. In the methods below, $R^0$, $R^1$, $R^2$, and $R^3$, are defined as in structural formula (I) above. In particular, Daugan U.S. Pat. No. 5,859,006, incorporated herein by reference, discloses preparation of a compound of structural formula (III)

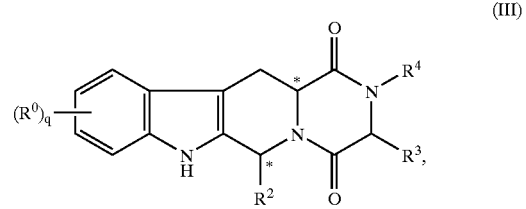

(III)

wherein $R^4$ is selected from the group consisting of hydrogen, $C_{1-6}$alkyl, $C_{2-6}$alkenyl, $C_{2-6}$alkynyl, halo$C_{1-6}$alkyl, $C_{3-8}$cycloalkyl, $C_{3-8}$cycloalkyl$C_{1-3}$alkyl, aryl$C_{1-3}$alkyl, and heteroaryl$C_{1-3}$alkyl.

Daugan U.S. Pat. No. 5,859,006 teaches the preparation of the compound of structural formula (III) from a compound having the structural formula (IV):

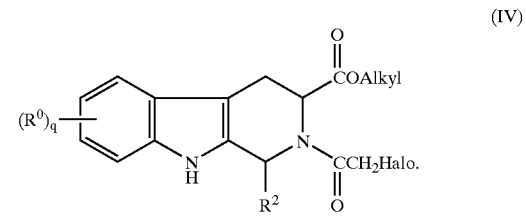

(IV)

The compounds of structural formula (I) can be prepared in an analogous manner as a compound of structural formula (III) using an appropriately $R^0$ and $R^2$ substituted compound of structural formula (IV) by the following exemplary synthetic sequence wherein $R^2$ is

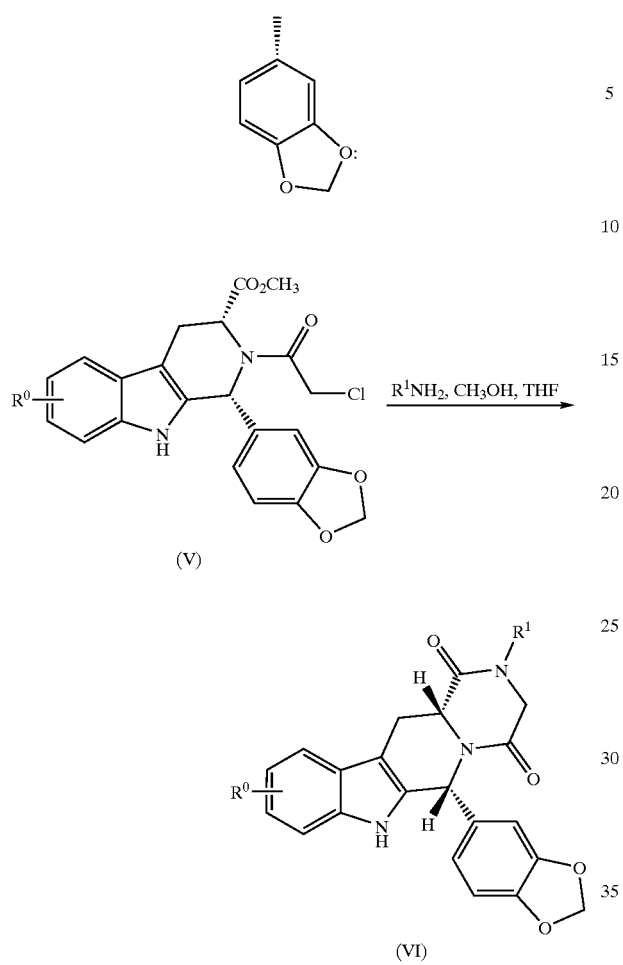

(V)

(VI)

Compound VI is synthesized by cyclization of the known chloro-compound (V) with a substituted amine in a suitable solvent to provide the diketopiperazine compound (VI).

Imide and N-acyl sulfonamide compounds are synthesized by treatment of an amide (VII), disclosed in U.S. Pat. No. 5,859,006 as Example 4, with an appropriately substituted acyl chloride (VII→VIII) or sulfonyl chloride (VII→IX) in methylene chloride and triethylamine catalyst:

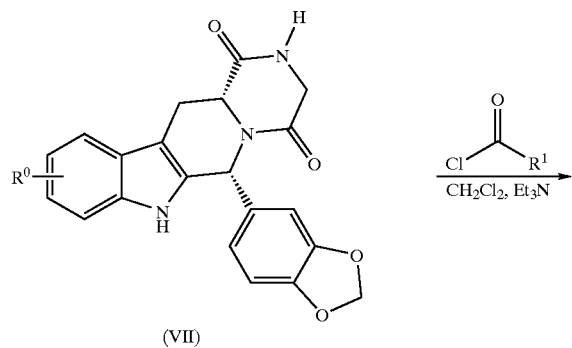

(VII)

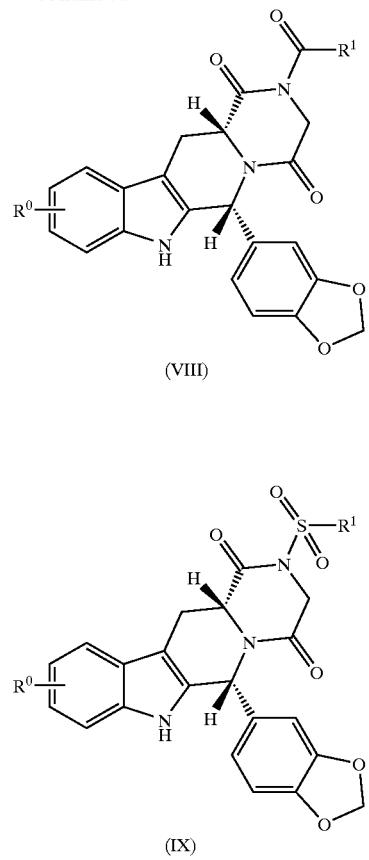

(VIII)

(IX)

Many substituted acyl chlorides and substituted sulfuryl chlorides are commercially available, and, if necessary, can be converted to other substituents after formation of compound (VIII) or (IX).

It should be understood that protecting groups can be utilized in accordance with general principles of organic synthetic chemistry to provide compounds of structural formula (I). Protecting compounds and protecting groups, like benzyl chloroformate and trichloroethyl chloroformate, are well known to persons skilled in the art, for example, see T. W. Greene et al., "Protective Groups in Organic Synthesis, Third Edition," John Wiley and Sons, Inc., NY, N.Y. (1999). These protecting groups are removed when necessary by appropriate basic, acidic, or hydrogenolytic conditions known to persons skilled in the art. Accordingly, compounds of structural formula (I) not specifically exemplified herein can be prepared by persons skilled in the art.

In addition, compounds of formula (I) can be converted to other compounds of formula (I). Thus, for example, a particular $R^1$ substituent can be interconverted to prepare another suitably substituted compound of formula (I). Examples of appropriate interconversions include, but are not limited to, $OR^a$ to hydroxy by suitable means (e.g., using an agent such as $SnCl_2$ or a palladium catalyst, like palladium-on-carbon), or amino to substituted amino, such as acylamino or sulphonylamino, using standard acylating or sulfonylating conditions.

Compounds of formula (I) can be prepared by the method above as individual stereoisomers from the appropriate stereoisomer of formula (IV) or as a racemic mixture from the appropriate racemic compound of formula (IV). Individual stereoisomers of the compounds of the invention can be prepared from racemates by resolution using methods known in the art for the separation of racemic mixtures into their constituent stereoisomers, for example, using HPLC on a chiral column, such as Hypersil naphthyl urea, or using separation of salts of stereoisomers. Compounds of the invention can be isolated in association with solvent molecules by crystallization from, or evaporation of, an appropriate solvent.

The pharmaceutically acceptable acid addition salts of the compounds of formula (I) that contain a basic center can be prepared in a conventional manner. For example, a solution of the free base can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of formula (I) with a suitable base. Both types of salt can be formed or interconverted using ion-exchange resin techniques. Thus, according to a further aspect of the invention, a method for preparing a compound of formula (I) or a salt or solvate (e.g., hydrate) is provided, followed by (i) salt formation, or (ii) solvate (e.g., hydrate) formation.

The following additional abbreviations are used hereafter in the accompanying examples: rt (room temperature), min (minute), h (hour), g (gram), mmol (millimole), m.p. (melting point), eq (equivalents), L (liter), mL (milliliter), μL (microliter), DMSO (dimethyl sulfoxide), $CH_2Cl_2$ (dichloromethane), IPA (isopropyl alcohol), TFA (trifluoroacetic acid), TEA (triethylamine), EtOH (ethanol), MeOH (methanol), DMF (dimethylformamide), $Et_3N$ (triethylamine), $MeNH_2$ (methylamine), AcOH (acetic acid), and THF (tetrahydrofuran).

PREPARATION OF EXAMPLE 1

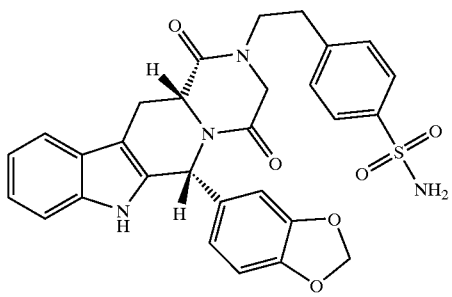

EXAMPLE 1

Example 1, and all other examples, were prepared using the following general method. All nonaqueous reactions were performed under a dry nitrogen atmosphere. Reagents and anhydrous solvents were purchased from commercial sources and used as received, unless otherwise noted. Melting points were obtained by differential scanning colorimetry (DSC) using a Perkin Elmer Model DSC-4 unit, or were obtained using an Electrothermal unit, and are uncorrected. Thin layer chromatography was performed using 1 inch×3 inch Analtech GF 350 silica gel plates with a fluorescent indicator. TLC plates were observed under a UV lamp, in iodine vapors, or by dipping in commercial phosphomolybdic acid solution, followed by warming. Infrared (IR) spectra were obtained on a single-beam Perkin-Elmer Spectrum 1000 FT-IR spectrometer using 4 accumulations at a resolution of 4.00 $cm^{-1}$ on samples prepared in a pressed disc of potassium bromide (KBr) or as a film on sodium chloride (NaCl) plates. Proton NMR spectra (300 MHz, referenced to tetramethylsilane) and carbon NMR spectra. (75 MHz, proton decoupled, referenced to residual solvent, signals) were obtained on a Bruker AC 300 spectrometer. Proton NMR spectra (500 MHz, referenced to tetramethylsilane) were obtained on a Bruker AMX 500 spectrometer. Mass spectra were obtained on a Shimadzu QP-5000 GC/MS mass spectrometer (CI mass spectrometry). Chiral HPLC analyses were obtained using a Chiracel OD column (250×4.6 mm) at ambient temperature with UV detection at 222 nm using an isochratic solvent system (1:1 isopropanol hexanes). Elemental analyses were performed by Quantitative Technologies, Inc., Whitehouse, N.J.

Example 1 was prepared from compound (V) ($R^0$=H, see Intermediate 2 in Example 2) by the following reaction:

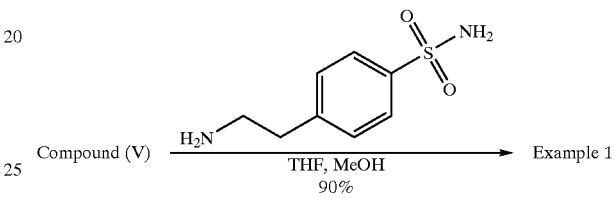

EXAMPLE 1

Preparation of (6R-trans)-6-(1,3-Benzodioxol-5-yl)-2,3,6,7,12,12a-hexahydro-2-[2-(4-phenylsulfamoyl)-ethyl]pyrazino[1',2':1,6]pyrido[3,4-b]indole-1,4-dione A mixture of Compound (V) (4.27 g, 10.0 mmol) and 4-(2-aminoethyl)benzenesulfonamide (4.0 g, 20 mmol) in methanol (50 mL) and THF (25 mL) was heated at 45° C. for 22 hours. The resulting clear solution was concentrated to dryness, and the residue was stirred in methanol (40 mL) for 20 minutes. The resulting white solid was collected by vacuum filtration, and washed with methanol (5×20 mL), followed by hexanes (3×20 mL), then dried in a vacuum oven at 40° C. to yield Example 1 as a white powder (5.0 g, 89.5%): TLC $R_f$ (3:1 methylene chloride/ethyl acetate)= 0.11; $^1$H NMR (300 MHz, DMSO-$d_6$): δ 11.08 (s, 1H), 7.75 (d, J=8.2 Hz, 2H), 7.54 (d, J=7.6 Hz, 1H), 7.43 (d, J=8.2 Hz, 2H), 7.31 (d, J=7.6 Hz, 1H), 7.30–6.91 (m, 4H), 6.89 (s, 1H), 6.85–6.70 (m, 2H), 6.16 (s, 1H), 5.94 (s, 2H), 4.41 (dd, J=11.5, 4.7 Hz, 1H), 4.17 (d, J=16.9 Hz, 1H), 3.97 (d, J=16.9 Hz, 1H), 3.73–3.50 (m, 2H), 3.48 (dd, J=15.8, 4.4 Hz, 1H), 3.05–2.81 (m, 3H); $^{13}$C NMR (125 MHz, DMSO-$d_6$): δ 167.1, 165.6, 147.1, 146.1, 143.0, 142.2, 137.0, 136.2, 133.9, 129.3, 125.8, 121.3, 119.0, 118.1, 111.3, 108.1, 106.9, 104.6, 101.0, 55.4, 55.1, 50.0, 48.5, 32.4, 22.1 ppm; API MS m/z 559 ($C_{29}H_{26}N_4O_6S$+H)$^+$; $[α]_D^{27°\ C.}$=+41.6° (c=1.0, DMSO). Anal. Calcd. for $C_{29}H_{26}N_4O_6S$: C, 62.35; H, 4.69; N, 10.03; S, 5.74. Found: C, 61.99; H, 4.76; N, 10.11; S, 5.81. The stereochemistry of Example 1 was confirmed to be the desired cis isomer by an NOE difference experiment (DMSO-$d_6$): positive NOE enhancements from the C12a proton at 4.41 ppm to the C6 proton at 6.16 ppm (0.5%) and a C12 proton at 3.48 ppm (3.4%).

PREPARATION OF EXAMPLE 2

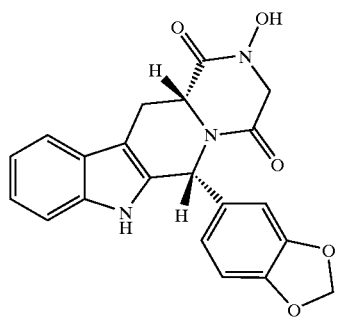

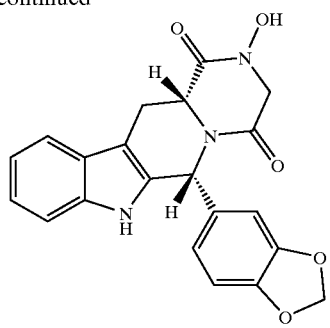

Example 2 was prepared from a starting tryptophan ester hydrochloride which is commercial available from Aldrich Chemical Co., Milwaukee, Wis. The reaction sequence is disclosed in Daugan U.S. Pat. No. 5,859,006, incorporated herein by reference. The reaction sequence include the steps of

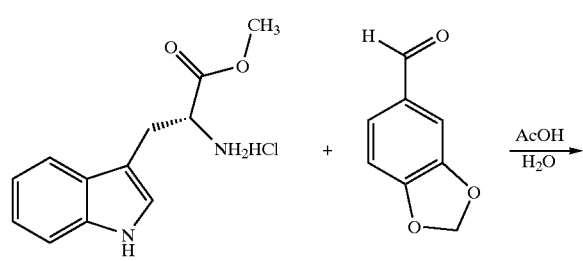

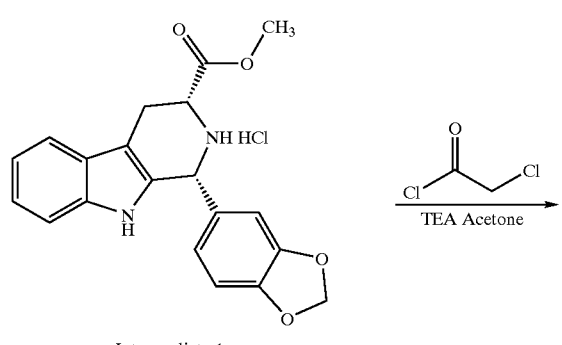
Intermediate 1

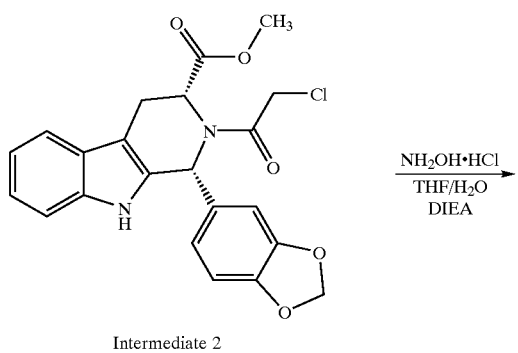
Intermediate 2

EXAMPLE 2

Preparation of Intermediate 1

(1R,3R)-1-Benzo[1,3]dioxol-5-yl-2,3,4,9-tetrahydro-1H-β-carboline-3-carboxylic Acid Methyl Ester Hydrochloride D-Tryptophan methyl ester hydrochloride (50.0 g, 0.196 mol, 0.5 eq) was suspended in 500 ml acetic acid, water (10 ml), then piperonal (88.0 g, 0.586 mol, 1.5 31) was added. The resulting mixture was stirred at 50° C. for 24 hours. A second charge of 50.0 g D-tryptophan methyl ester hydrochloride then was added to the clear solution. After 73 hours, the resulting suspension was cooled to ambient temperature and diluted with 1.2 L ethyl acetate followed by 300 ml methyl t-butyl ether. The mixture then was cooled in an ice bath, the solid collected by filtration, rinsed with 2×100 ml methyl t-butyl ether, and dried in vacuo to yield 90.2 g (59% yield) of Intermediate 1 as a white solid: mp 215–216° C.; $^1$H NMR (DMSO-$d_6$): δ 10.85 (s, 1H), 10.55 (br s, 1H), 10.12 (br s, 1H), 7.54 (d, J=7.6, 1H), 7.29 (d, J=7.9, 1H), 7.14–7.01 (m, 4H), 6.97 (s, 1H), 6.10 (s, 2H), 5.86 (br s, 1H), 4.76 (m, 1H), 3.85 (s, 3H), 3.37 (d of d, $J_1$=15.9, $J_2$=4.8, 1H), 3.24 (t, J=13.6, 1H); MS m/z 351 (M+H); $[\alpha]_D^{21°\,C.}$=−54.8 (c=0.5, DMSO); Anal. Calcd. for $C_{20}H_{18}N_2O_4$·HCl: C, 62.10; H, 4.95; N, 7.24. Found: C, 61.33; H, 4.98; N, 7.03.

Preparation of Intermediate 2

(1R,3R)-1-Benzo[1,3]dioxol-5-yl-2-(2-chloroethanoyl)2,3,4,9-tetrahydro-1H-β-carboline-3-carboxylic Acid Methyl Ester Intermediate 1 (60.0 g, 0.155 mol) was suspended in 60 ml acetone. Triethylamine (36.0 g, 0.356 mol, 2.3 eq) then was added to the suspension. The resulting mixture was cooled to 0° C. in an ice bath, then chloroacetyl chloride (22.8 g, 0.202 mol, 1.3 eq) was added over 2 hours with stirring. The mixture was stirred at ambient temperature for an additional 1.5 hours, then 1.2 L water was added to slowly precipitate a solid. The mixture was cooled to 0° C. and held for 1 hour. The solid then was collected by vacuum filtration and washed with water. The solid was triturated with isopropyl alcohol, collected by filtration, and washed with portions of IPA. The resulting pale yellow solid (Intermediate 2) was dried in vacuo to yield 58.1 g (88% yield): mp 207–208° C.; $^1$H NMR (DMSO-$d_6$): δ 10.89 (s, 1H), 7.55 (d, J=7.6, 1H), 7.29 (d, J=7.9, 1H), 7.10 (t, J=7.1, 1H), 7.03 (t, J=7.1, 1H), 6.81 (d, J=8.1, 1H), 6.76 (s, 1H), 6.64 (s, 1H), 6.45 (d, J=7.1, 1H), 5.98 (d, J=6.1, 2H), 5.20 (d, J=6.5, 1H), 4.85 (d, J=13.9, 1H), 4.45 (d, J=13.9, 1H), 3.47 (d, J=15.9, 1H), 3.08 (d of d, $J_1$=16.3, $J_2$=7.0, 1H), 3.04 (s, 3H); MS m/z 427 (M+H); $[\alpha]_D^{23°\,C.}$=−120.9 (c=0.5, DMSO); Anal. Calcd. for $C_{22}H_{19}N_2O_5$Cl: C, 61.43; H, 4.49; N, 6.56. Found: C, 61.82; H, 4.45; N, 6.55.

17

PREPARATION OF EXAMPLE 2

(6R,12aR)-6-Benzo[1,3]dioxo-5-yl-2-hydroxy-2,3,6,7,12,12a-hexahydropyrazino[1',2':1,6]-pyrido[3,4-b]indole-1,4-dione Intermediate 2 (3.45 g, 8.08 mmol) and hydroxylamine hydrochloride (1.12 g, 16.2 mmol) were suspended in tetrahydrofuran. While stirring, 3.5 ml water and then 2.82 ml (16.2 mmol) diisopropylethylamine were added to the mixture. The resulting mixture was heated at 45° C. in an oil bath for 24 hours. The reaction mixture was allowed to cool to room temperature, then was poured into ethyl acetate, washed with saturated NaCl, dried over sodium sulfate ($Na_2SO_4$), filtered, and the solvent stripped on a rotary evaporator. The resulting residue was recrystallized from ethyl acetate to yield 2.09 g (66%) of Example 2 as an off-white solid: mp=276–283° C. (dec.); $^1H$ NMR (DMSO-$d_6$): δ 10.99 (s, 1H), 10.23 (s, 1H), 7.55 (d, J=7.4, 1H), 7.29 (d, J=7.8, 1H), 7.06 (t, J=7.3, 1H), 6.99 (t, J=7.5, 1H), 6.88 (s, 1H), 6.84–6.77 (m, 2H), 6.05 (s, 1H), 5.93 (d, J=2.3, 2H), 4.45 (d of d, $J_1$=12.1, $J_2$=4.0, 1H), 4.39 (d, J=19.9, 1H), 4.10 (d, J=16.4, 1H), 3.57 (d of d, $J_1$=15.3, $J_2$=11.9, 1H); MS m/z 332 (M+H), 414 (M+Na); $[α]_D^{27° \ C.}$=106.6 (c=0.05, DMSO); Anal. Calcd. for $C_{21}H_{17}N_3O_5$; C, 64.45; H, 4.38; N, 10.74. Found: C, 64.14; H, 4.55; N, 10.55. Stereochemistry was confirmed by NOE experiments: Positive NOE enhancements observed from C12a (4.39 ppm) to C6 (6.05 ppm) and from C6 to C12a.

PREPARATION OF EXAMPLE 3

(6R,12aR)-6-Benzo[1,3]dioxol-5-yl-2-methoxy-2,3,6,7,12,12a-hexahydropyrazino[1',2':1,6]-pyrido[3,4-b]indole-1,4-dione

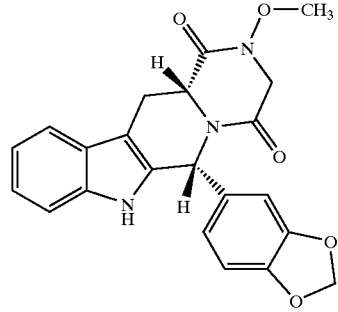

Example 3 was prepared directly from Example 2 as follows:

Example 2 (0.278 g, 0.710 mmol) was added to a dried flask and maintained under a nitrogen atmosphere. Example 2 was suspended in anhydrous dimethylformamide, then dry $K_2CO_3$ (0.247 g, 1.79 mmol) was added followed by 0.049 ml (0.78 mmol) methyl iodide. The resulting mixture was stirred magnetically under a nitrogen blanket for 24 hours. The reaction then was diluted with ethyl acetate and washed with saturated sodium bicarbonate ($NaHCO_3$), 1N hydrochloric acid (HCl), and saturated NaCl, dried over $Na_2SO_4$, filtered and the solvent stripped on a rotary evaporator. The resulting residue was purified by flash chromatography ($CH_2Cl_2$/ethyl acetate/methanol (90:10:1) followed by recrystallization (methanol) to yield, after drying, 79 mg (27% yield) of Example 3 as a white crystalline solid: mp=268–270° C.; TLC $R_f$ ($CH_2Cl_2$/ethyl acetate/methanol)=0.24; $^1H$ NMR (DMSO-$d_6$): δ 10.95 (s, 1H), 7.54 (d, J=7.3, 1H), 7.28 (d, J=7.7, 1H), 7.05 (t, J=7.6; 1H), 6.99 (t, J=7.6, 1H), 6.88 (s, 1H), 6.84–6.77 (m, 2H), 6.03 (s, 1H), 5.92 (d, J=3.9, 2H), 4.43 (d of d, $J_1$=11.7, $J_2$=3.8, 1H), 4.40 (d, J=14.6, 1H), 4.31 (d, J=16.1, 1H), 3.76 (s, 3H), 3.55 (d of d, $J_1$=15.7, $J_2$=4.1, 1H), 3.02 (d of d, $J_1$=15.0, $J_2$=11.8, 1H); MS m/z 406 (M+H), 428 (M+Na); $[α]_D^{25° \ C.}$=91.7 (c=0.1, DMSO); Anal. Calcd. for $C_{22}H_{19}N_3O_5$: C, 65.18; H, 4.72; N, 10.36. Found: C, 64.87; H, 4.60; N, 10.27. Stereochemistry was confirmed by NOE experiments: Positive NOE enhancements observed from C12a (4.43 ppm) to C6 (6.03 ppm) and from C6 to C12a.

PREPARATION OF EXAMPLE 4

(6R,12aR)-2-Amino-6-benzo[1,3]dioxo-5-yl-2,3,6,7,12,12a-hexahydropyrazino[1', 2':1,6]-pyrido[3,4-b]indole-1,4-dione Example 4 was prepared in one step from Intermediate 2 as follows:

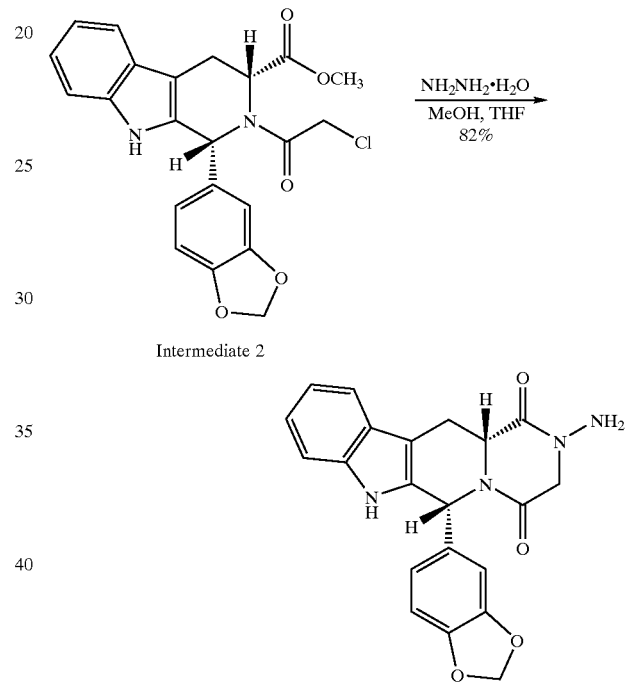

EXAMPLE 4

A mixture of Intermediate 2 (2.14 g, 5 mmol) and hydrazine hydrate (1.2 mL, 25 mmol) in methanol (20 mL) was stirred at room temperature under a nitrogen blanket for 2 days. To aid solubility, THF (7 mL) was added to the mixture, and the resulting mixture was stirred at room temperature for an additional 2.5 days. The white solid was collected by vacuum filtration, washed with methanol (10×5 mL), then dried in a vacuum oven at 60° C. for 2 days to yield Example 4 as a white powder (1.6 g, 82%), which was confirmed to be the desired cis isomer by NOE analysis (2.4% enhancement): mp 272–278° C.; TLC $R_f$ (4:1:0.5 methylene chloride/ethyl acetate/methanol)=0.49; $^1H$ NMR (300 MHz, DMSO-$d_6$): δ 11.01 (s, 1H), 7.55 (d, J=7.5 Hz, 1H), 7.30 (d, J=7.5 Hz, 1H), 7.09–6.98 (m, 2H), 6.89–6.76 (m, 3H), 6.11 (s, 1H), 5.93 (s, 2H), 5.12 (s, 2H), 4.47–4.42 (m, 1H), 4.27 (d, J=17.0 Hz, 1H), 3.97 (d, J=17.0 Hz, 1H), 3.61–3.55 (m, 1H), 3.04–2.95 (m, 1H); $^{13}C$ NMR (75 MHz, DMSO-$d_6$): δ 166.2, 164.6, 147.0, 146.0, 137.0, 136.2, 133.9, 125.7, 121.2, 119.3, 118.8, 118.0, 111.2, 107.9, 106.9, 104.8, 100.8, 55.5, 55.3, 53.3, 23.3 ppm; CI MS (methane) m/z 391 [M+H]$^+$; $[\alpha]_D^{25°\,C.}$=+75.7 (c=1.0, DMSO). Anal. Calcd. for $C_{21}H_{20}N_4O_3$; C, 64.61; H, 4.65; N, 14.35. Found: C, 64.41; H, 4.56; N, 14.31.

The following Examples 5 and 7–88 were prepared by methods analogous to Examples 1–4.

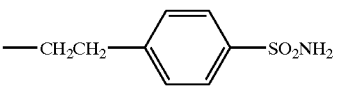

| Example | R$^1$ | R$^{2\,1)}$ | R$^3$ |
|---|---|---|---|
| 1 | —CH$_2$CH$_2$—C$_6$H$_4$—SO$_2$NH$_2$ | 1 | H |
| 2 | —OH | 1 | H |
| 3 | —OCH$_3$ | 1 | H |
| 4 | —NH$_2$ | 1 | H |
| 5 | —NHCH$_3$ | 1 | H |
| 7 | —C$_6$H$_5$ | 1 | H |
| 8 | —CH$_2$CH$_2$N(CH$_3$)$_2$ | 1 | CH$_3$ |
| 9 | —CH$_2$CH$_2$N(CH$_3$)$_2$ | 2 | H |
| 10 | —CH$_2$CH$_2$OH | 1 | H |
| 11 | —(CH$_2$)$_3$N(CH$_3$)$_2$ | 2 | H |
| 12 | —(CH$_2$)$_3$—N(piperazine)—CH$_3$ | 2 | H |
| 13 | —(CH$_2$)$_2$—N(piperidine) | 1 | H |
| 14 | —(CH$_2$)$_2$—N(CH$_2$CH$_3$)$_2$ | 1 | H |
| 15 | —(CH$_2$)$_2$—N(morpholine) | 1 | H |
| 16 | —(CH$_2$)$_2$—N(morpholine) | 1 | H |
| 17 | —(CH$_2$)$_2$—N(morpholine) | 2 | H |
| 18 | —(CH$_2$)$_3$—N(morpholine) | 1 | H |
| 19 | —CH$_2$C(=O)OCH$_3$ | 1 | H |
| 20 | —CH$_2$C(=O)NH$_2$ | 1 | H |

-continued

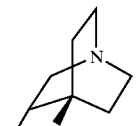

| Example | R$^1$ | R$^{2\,1)}$ | R$^3$ |
|---|---|---|---|
| 21 | (quinuclidinyl) | 1 | H |
| 22 | —(CH$_2$)N(CH(CH$_3$)$_2$)$_2$ | 1 | H |
| 23 | (quinuclidinyl) | 1 | H |
| 24 | —(CH$_2$)$_2$C(=O)OCH$_2$CH$_3$ | 1 | H |
| 25 | —(CH$_2$)$_3$OCH$_3$ | 1 | H |
| 26 | —(CH$_2$)$_2$NHC(=O)CH$_3$ | 1 | H |
| 27 | —(CH$_2$)$_3$—N(2-pyrrolidinone) | 1 | H |
| 28 | —CH$_2$C(=O)NH—C$_6$H$_5$ | 1 | H |
| 29 | —(CH$_2$)$_2$OCH$_3$ | 1 | H |
| 30 | —CH$_2$C(=O)NHCH$_2$—C$_6$H$_5$ | 1 | H |
| 31 | —CH$_2$C(=O)—N(piperidine) | 1 | H |
| 32 | —(CH$_2$)$_3$—N(imidazole) | 1 | H |
| 33 | —(CH$_2$)$_2$C(=O)NH—C$_6$H$_{11}$ | 1 | H |
| 34 | —(CH$_2$)$_3$C(=O)N(CH$_3$)—(CH$_2$)$_3$CH$_3$ | 1 | H |
| 35 | —(CH$_2$)$_3$C(=O)NH—C$_6$H$_{11}$ | 1 | H |
| 36 | —(CH$_2$)$_2$C(=O)OH | 1 | H |
| 37 | —CH$_2$—(tetrahydrofuran-2-yl) | 1 | H |

-continued

![Structure 21: tetracyclic indole-fused piperazinedione with (R⁰)q on benzene ring, R¹ on amide N, R² at ring junction (wedge), R³ at adjacent position]

| Example | R¹ | R² ¹⁾ | R³ |
|---|---|---|---|
| 38 | —CH₂C(=O)NH—(4-pyridyl) | 1 | H |
| 39 | —(CH₂)₃OCH₂CH₃ | 1 | H |
| 40 | —(CH₂)₂O(CH₂)₂OH | 1 | H |
| 41 | —CH₂CH(OH)CH₃ | 1 | H |
| 42 | —CH₂C(=O)—N(piperazine)N—C₆H₅ | 1 | H |
| 43 | —CH₂C(=O)N(CH₃)—C₆H₅ | 1 | H |
| 44 | quinuclidinyl-CH₂CH₂— | 1 | H |
| 45 | —CH₂-(2-benzimidazolyl) | 1 | H |
| 46 | —(CH₂)₂—N(piperazine)N—CH₃ | 1 | H |
| 47 | —CH₂—C₆H₄—C(=O)OH | 1 | H |
| 48 | —CH₂—C₆H₄—N(CH₃)₂ | 1 | H |
| 49 | —CH₂—C₆H₄—N(CH₃)₂ | 1 | CH₃ |
| 50 | —(CH₂)₂—N(2,6-dimethylmorpholinyl) | 1 | H |

-continued

![Structure 22: same as 21 but with R² shown on opposite wedge (stereoisomer)]

| Example | R¹ | R² ¹⁾ | R³ |
|---|---|---|---|
| 51 | —(CH₂)₂—N(2,6-dimethylmorpholinyl) | 1 | H |
| 52 | —(CH₂)₂—N(2,6-dimethylmorpholinyl) | 2 | H |
| 53 | —(CH₂)₂—N(imidazolyl) | 1 | H |
| 54 | —(CH₂)₂—N(2-methyl-pyrrolyl) | 1 | H |
| 55 | —(CH₂)₂—N(imidazolyl) | 1 | H |
| 56 | —CH₂—C₆H₄—NH₂ | 1 | H |
| 57 | —CH₂—C₆H₄—NHSO₂CF₃ | 1 | H |
| 58 | —CH₂—C₆H₄—SO₂NH₂ | 1 | H |
| 59 | —CH₂—C₆H₄—CN | 1 | H |
| 60 | —CH₂CN | 1 | H |
| 61 | —CH₂-(2-benzimidazolyl) | 1 | H |

-continued

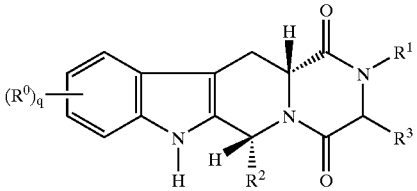

| Example | R¹ | R² 1) | R³ |
|---|---|---|---|
| 62 | —CH₂—C₆H₄—C(=O)OCH₃ | 1 | H |
| 63 | —(CH₂)₂—(N-methylpyrrolidin-2-yl) | 1 | H |
| 64 | —(CH₂)₂—(1H-imidazol-4-yl) | 1 | H |
| 65 | —CH₂—C₆H₄—CH₂N(CH₃)₂ | 1 | H |
| 66 | —(CH₂)₂—C₆H₄—NH₂ | 1 | H |
| 67 | —(CH₂)₂—C₆H₄—SO₂NH₂ | 1 | H |
| 68 | —CH₂C(=O)OCH₂C₆H₅ | 1 | H |
| 69 | —CH₂C(=O)OH | 1 | H |
| 70 | —(CH₂)₃—(3,5-dimethylpyrazol-1-yl) | 1 | H |
| 71 | —(CH₂)₂C(=O)OC(CH₃)₃ | 1 | H |
| 72 | —(CH₂)₂C(=O)OH | 1 | H |
| 73 | —CH₂—C₆H₄—CH₂N(CH₃)₂ | 1 | H |
| 74 | —(CH₂)₂—(pyrazol-1-yl) | 1 | H |
| 75 | —CH₂—C₆H₄—NO₂ | 1 | H |

-continued

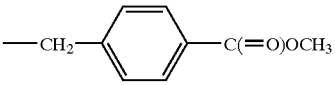

| Example | R¹ | R² 1) | R³ |
|---|---|---|---|
| 76 | —CH₂—C₆H₄—NH₂ | 1 | H |
| 77 | —CH₂—C₆H₄—NHSO₂CF₃ | 1 | H |
| 78 | —(CH₂)₂—(pyrazol-1-yl) | 1 | H |
| 79 | —(CH₂)₃—(pyrazol-1-yl) | 1 | H |
| 80 | —CH₂—C₆H₄—OCH₂C₆H₅ | 1 | H |
| 81 | —CH₂—C₆H₄—OCH₂CH₂N(CH₃)₂ | 1 | H |
| 82 | —CH₂CH₂—(1,2,4-triazol-1-yl) | 1 | H |
| 83 | —CH₂—C₆H₃(NHCH₃)(NO₂) | 1 | H |
| 84 | —CH₂C(=O)NH—(4-methylpiperazin-1-yl) | 1 | H |
| 85 | —CH₂—(1-methylbenzimidazol-5-yl) | 1 | H |
| 86 | —CH₂C(=O)OC(CH₃)₃ | 1 | H |
| 87 | —CH₂C(=O)OCH₃ | 1 | H |
| 88 | —CH₂C(=O)O(CH₂)₇CH₃ | 1 | H |

1)for R², the designation 1 is

-continued

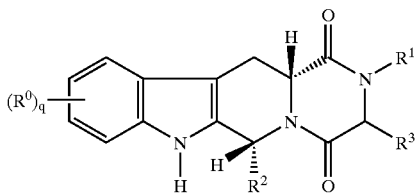

| Example | $R^1$ | $R^2$ 1) $R^3$ |
|---|---|---|

![structure with benzodioxole substituent attached via dashed bond, showing O—CH₂ bridge]

and the designation 2 is

![structure showing phenyl with OCH₃ substituent attached via dashed bond]

Compounds of the present invention can be formulated into tablets for oral administration. For example, a compound of formula (I) can be formed into a dispersion with a polymeric carrier by the coprecipitation method set forth in WO 96/38131, incorporated herein by reference. The coprecipitated dispersion then can be blended with excipients, then pressed into tablets, which optionally are film-coated.

The compounds of structural formula (I) were tested for an ability to inhibit PDE5. The ability of a compound to inhibit PDE5 activity is related to the $IC_{50}$ value for the compound, i.e., the concentration of inhibitor required for 50% inhibition of enzyme activity. The $IC_{50}$ value for compounds of structural formula (I) were determined using recombinant human PDE5.

The compounds of the present invention typically exhibit an $IC_{50}$ value against recombinant human PDE5 of less than about 50 $\mu$M, and preferably less than about 25 $\mu$M, and more preferably less than about 15 $\mu$m. The compounds of the present invention typically exhibit an $IC_{50}$ value against recombinant human-PDE5 of less than about 1 $\mu$M, and often less than about 0.05 $\mu$M. To achieve the full advantage of the present invention, a present PDE5 inhibitor has an $IC_{50}$ of about 0.1 nM to about 15 $\mu$M.

The production of recombinant human PDEs and the $IC_{50}$ determinations can be accomplished by well-known methods in the art. Exemplary methods are described as follows:
Expression of Human PDEs
Expression in *Saccharomyces cerevisiae* (Yeast)

Recombinant production of human PDE1B, PDE2, PDE4A, PDE4B, PDE4C, PDE4D, PDE5, and PDE7 was carried out similarly to that described in Example 7 of U.S. Pat. No. 5,702,936, incorporated herein by reference, except that the yeast transformation vector employed, which is derived from the basic ADH2 plasmid described in Price et al., *Methods in Enzymology*, 185, pp. 308–318 (1990), incorporated yeast ADH2 promoter and terminator sequences and the *Saccharomyces cerevisiae* host was the protease-deficient strain BJ2-54 deposited on Aug. 31, 1998 with the American Type Culture Collection, Manassas, Va., under accession number ATCC 74465. Transformed host cells were grown in 2×SC-leu medium, pH 6.2, with trace metals, and vitamins. After 24 hours, YEP medium-containing glycerol was added to a final concentration of 2×YET/3% glycerol. Approximately 24 hr later, cells were harvested, washed, and stored at −70° C.
Human Phosphodiesterase Preparations
Phosphodiesterase Activity Determinations Phosphodiesterase activity of the preparations was determined as follows. PDE assays utilizing a charcoal separation technique were performed essentially as described in Loughney et al. (1996). In this assay, PDE activity converts [32P]cAMP or [32P]cGMP to the corresponding [32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5'-nucleotidase. Hence, the amount of [32P]phosphate liberated is proportional to enzyme activity. The assay was performed at 30° C. in a 100 $\mu$L reaction mixture containing (final concentrations) 40 mM Tris HCl (pH 8.0), 1 $\mu$M $ZnSO_4$, 5 mM $MgCl_2$, and 0.1 mg/mL bovine serum albumin (BSA). PDE enzyme was present in quantities that yield <30% total hydrolysis of substrate (linear assay conditions). The assay was initiated by addition of substrate (1 mM [32P]cAMP or cGMP), and the mixture was incubated for 12 minutes. Seventy-five (75) $\mu$g of Crotalus atrox venom then was added, and the incubation was continued for 3 minutes (15 minutes total). The reaction was stopped by addition of 200 $\mu$L of activated charcoal (25 mg/mL suspension in 0.1 M $NaH_2PO_4$, pH 4). After centrifugation (750×g for 3 minutes) to sediment the charcoal, a sample of the supernatant was taken for radioactivity determination in a scintillation counter and the PDE activity was calculated.
Purification of PDE5 from *S. cerevisiae*

Cell pellets (29 g) were thawed on ice with an equal volume of Lysis Buffer (25 mM Tris HCl, pH 8, 5 mM $MgCl_2$, 0.25 mM DTT, 1 mM benzamidine, and 10 $\mu$M $ZnSO_4$). Cells were lysed in a Microfluidizer® (Microfluidics Corp.) using nitrogen at 20,000 psi. The lysate was centrifuged and filtered through 0.45 $\mu$m disposable filters. The filtrate was applied to a 150 mL column of Q SEPHAROSE® Fast-Flow (Pharmacia). The column was washed with 1.5 volumes of Buffer A (20 mM Bis-Tris Propane, pH 6.8, 1 mM $MgCl_2$, 0.25 mM DTT, 10 $\mu$M $ZnSO_4$) and eluted with a step gradient of 125 mM NaCl in Buffer A followed by a linear gradient of 125–1000 mM NaCl in Buffer A. Active fractions from the linear gradient were applied to a 180 mL hydroxyapatite column in Buffer B (20 mM Bis-Tris Propane (pH 6.8), 1 mM $MgCl_2$, 0.25 mM DTT, 10 $\mu$M $ZnSO_4$, and 250 mM KCl). After loading, the column was washed with 2 volumes of Buffer B and eluted with a linear gradient of 0–125 mM potassium phosphate in Buffer B. Active fractions were pooled, precipitated with 60% ammonium sulfate, and resuspended in Buffer C (20 mM Bis-Tris Propane, pH 6.8, 125 mM NaCl, 0.5 mM DTT, and 10 $\mu$M $ZnSO_4$). The pool was applied to a 140 mL column of SEPHACRYL® S-300 HR and eluted with Buffer C. Active fractions were diluted to 50% glycerol and stored at −20° C.

The resultant preparations were about 85% pure by SDS-PAGE. These preparations had specific activities of about 3 $\mu$mol CGMP hydrolyzed per minute per milligram protein.
Inhibitory Effect on cGMP-PDE cGMP-PDE activity of compounds of the present invention was measured using a one-step assay adapted from Wells et al., *Biochim. Biophys. Acta*, 384, 430 (1975). The reaction medium contained 50 mM Tris-HCl, pH 7.5, 5 mM magnesium acetate, 250 μg/ml 5'-Nucleotidase, 1 mM EGTA, and 0.15 μM 8-[$H^3$]-cGMP. Unless otherwise indicated, the enzyme used was a human recombinant PDE5 (ICOS Corp., Bothell, Wash.).

Compounds of the invention were dissolved in DMSO finally present at 2% in the assay. The incubation time was 30 minutes during which the total substrate conversion did not exceed 30%.

The $IC_{50}$ values for the compounds examined were determined from concentration-response curves typically using concentrations ranging from 10 nM to 10 μM. Tests against other PDE enzymes using standard methodology showed that compounds of the invention are selective for the cGMP-specific PDE enzyme.

Biological Data

The compounds according to the present invention were typically found to exhibit an $IC_{50}$ value of less than 500 nM (i.e., 0.5 μM). In vitro test data for representative compounds of the invention is given in the following table:

TABLE 1

In vitro Results

| Example | PDE5 $IC_{50}$ (μM) |
|---|---|
| 1 | 0.0014 |
| 2 | 0.0075 |
| 3 | 0.0025 |
| 4 | 0.0018 |
| 7 | 0.0062 |
| 8 | 0.13 |
| 9 | 0.07 (Bov. aorta)[1] |
| 10 | 0.005 (Bov. aorta) |
| 11 | 0.65 (Bov. aorta) |
| 12 | 0.1 (Bov. aorta) |
| 13 | 0.25 (Bov. aorta) |
| 14 | 0.08 (Bov. aorta) |
| 15 | 0.06 (Bov. aorta) |
| 16 | 0.01 (stereoisomer of Ex. 15) |
| 17 | 0.01 |
| 18 | 0.04 |
| 19 | 0.004 (Bov. aorta) |
| 20 | 0.01 (Bov. aorta) |
| 21 | 0.16 (Bov. aorta) |
| 22 | 0.47 |
| | 1.61 (Bov. aorta) |
| 23 | 0.12 |
| | 0.41 (Bov. aorta) |
| 24 | 0.0096 |
| 25 | 0.01 |
| 26 | 0.01 |
| 27 | 0.0054 |
| 28 | 0.0039 |
| 29 | 0.0059 |
| 30 | 0.02 |
| 31 | 0.02 |
| 32 | 0.01 |
| 33 | 0.01 |
| 34 | 0.01 |
| 35 | 0.0043 |
| 36 | 0.05 |
| 37 | 0.03 |
| 38 | 0.0039 |
| 39 | 0.03 |
| 40 | 0.01 |
| 41 | 0.02 |
| 42 | 0.14 |
| 43 | 0.1 |
| 44 | 0.4 |
| 45 | 0.08 |
| 46 | 0.05 |
| 47 | 0.0043 |
| 48 | 0.02 |
| 49 | 0.07 |
| 50 | 52.1 (Bov. aorta) |

TABLE 1-continued

In vitro Results

| Example | PDE5 $IC_{50}$ (μM) |
|---|---|
| 51 | 0.0059 (stereoisomer of Ex. 50) |
| 52 | 0.01 |
| 53 | 0.55 |
| 54 | 0.09 |
| 55 | 0.05 |
| 56 | 0.0042 |
| 57 | 0.0051 |
| 58 | 0.02 |
| 59 | 0.07 |
| 60 | 0.01 |
| 61 | 0.01 |
| 62 | 0.02 |
| 63 | 0.13 |
| 64 | 0.02 |
| 65 | 0.63 |
| 66 | 0.04 |
| 67 | 0.0062 |
| 68 | 0.04 |
| 69 | 0.02 |
| 70 | 0.0084 |
| 71 | 0.01 |
| 72 | 0.0023 |
| 73 | 0.09 |
| 75 | 0.05 |
| 76 | 0.0088 |
| 77 | 0.0017 |
| 78 | 0.1 |
| 79 | 0.0063 |
| 80 | 0.07 |
| 81 | 0.29 |
| 82 | 0.03 |
| 83 | 0.04 |
| 84 | 0.12 |
| 85 | 0.02 |
| 86 | 0.07 |
| 87 | 0.02 |
| 88 | 0.11 |

[1]$IC_{50}$ determination made using PDE5 obtained from bovine aorta.

Obviously, many modifications and variations of the invention as hereinbefore set forth can be made without departing from the spirit and scope thereof, and, therefore, only such limitations should be imposed as are indicated by the appended claims.

What is claimed is:

1. A compound selected from the group consisting of 4-[2-((6R,12aR)-6-benzo[1,3]dioxol-5-yl--1,4-dioxo-3,4,6,7,12,12a-hexahydro-1H-pyrazino-[1',2':1,6]-pyrido[3,4-b]indol-2-yl)ethyl]-benzenesulfonamide;

(6R,12aR)-6-benzo[1,3]dioxo-5-yl-2-hydroxy-2,3,6,7,12,12a-hexahydropyrazino[1',2':1,6]pyrido[3,4-b]indole-1,4-dione;

(6R,12aR)-6-benzo[1,3]dioxol-5-yl-2-methoxy-2,3,6,7,12,12a-hexahydropyrazino[1',2':1,6]pyrido[3,4-b]indole-1,4-dione;

(6R,12aR)-2-amino-6-benzo[1,3]dioxo-5-yl-1,2,6,7,12,12a-hexahydropyrazino[1',2':1,6]pyrido[3,4-b]indole-1,4-dione;

(6R,12aR)-6-benzo[1,3]dioxol-5-yl-2-methylamino-2,3,6,7,12,12a-hexahydropyrazino-[1',2':1,6]-pyrido[3,4-b]indole-1,4-dione;

(6R,12aR)-6-benzo[1,3]dioxol-5-yl-2-phenyl-2,3,6,7,12,12a-hexahydropyrazino[1',2':1,6]pyrido[3,4-b]indole-1,4-dione;

(6R,12aR)-6-benzo[1,3]dioxol-5-yl-2-(2-dimethylaminoethyl)-3-methyl-2,3,6,7,12,12a-hexahydropyrazino[1',2':1,6]pyrido[3,4-b]indole-1,4-dione;

(+−,cis)-2-(2-dimethylamino-ethyl)-6-(4-methoxy-phenyl)-2,3,6,7,12,12a-hexahydropyrazino-[1',2':1,6]pyrido[3,4-b]indole-1,4-dione;

(+−,cis)-6-benzo[1,3]dioxol-5-yl-2-(2-hydroxyethyl)-2,3,6,7,12,12a-hexahydropyrazino-[1',2':1,6]pyrido[3,4-b]indole-1,4-dione;

(+−,cis)-2-(3-dimethylaminopropyl)-6-(4-methoxyphenyl)-2,3,6,7,12,12a-hexahydropyrazino-[1',2':1,6]pyrido[3,4-b]indole-1,4-dione;

(+−,cis)-6-(4-methoxyphenyl)-2-[3-(4-methylpiperazin-1-yl)propyl]-2,3,6,7,12,12a-hexahydropyrazino[1',2':1,6]pyrido[3,4-b]indole-1,4-dione;

(+−,cis)-6-benzo[1,3]dioxol-5-yl-2-(2-piperidin-1-ylethyl)-2,3,6,7,12,12a-hexahydropyrazino-[1',2':1,6]pyrido[3,4-b]indole-1,4-dione;

(+−,cis)-6-benzo[1,3]dioxol-5-yl-2-(-2-diethylaminoethyl)-2,3,6,7,12,12a-hexahydropyrazino-[1',2':1,6]pyrido[3,4-b]indole-1,4-dione;

(+−,cis)-6-benzo[1,3]dioxol-5-yl-2-(2-morpholin-4-ylethyl)-2,3,6,7,12,12a-hexahydropyrazino-[1',2':1,6]pyrido[3,4-b]indole-1,4-dione;

(6R,12aR)-6-benzo[1,3]dioxol-5-yl-2-(2-morpholin-4-ylethyl)-2,3,6,7,12,12a-hexahydropyrazino-[1',2':1,6]pyrido[3,4-b]indole-1,4-dione;

(6R,12aR)-6-(4-methoxyphenyl)-2-(2-morpholin-4-ylethyl)-2,3,6,7,12,12a-hexahydropyrazino[1',2':1,6]pyrido[3,4-b]indole-1,4-dione;

(6R,12aR)-6-benzo[1,3]dioxol-5-yl-2-(3-morpholin-4-ylpropyl)-2,3,6,7,12,12a-hexahydropyrazino-[1',2':1,6]pyrido[3,4-b]indole-1,4-dione;

(+−,cis)-6-benzo[1,3]dioxol-5-yl-1,4-dioxo-3,4,6,7,12,12a-hexahydro-1H-pyrazino-[1',2':1,6]pyrido-[3,4-b]indole-2-yl)acetic acid methyl ester;

2-((+−,cis)-6-benzo[1,3]dioxol-5-yl-1,4-dioxo-3,4,6,7,12,12a-hexahydro-1H-pyrazino[1',2':1,6]pyrido[3,4-b]indol-2-yl)-acetamide;

(+−,cis)-2-(1-azabicyclo[2.2.2]oct-3-yl)-6-benzo[1,3]dioxol-5-yl-2,3,6,7,12,12a-hexahydropyrazino-[1',2':1,6]pyrido[3,4-b]indole-1,4-dione;

(+−,cis)-6-benzo[1,3]dioxol-5-yl-2-(2-diisopropylaminoethyl)-2,3,6,7,12,12a-hexahydropyrazino-[1',2':1,6]pyrido[3,4-b]indole-1,4-dione;

(+−,cis)-2-(1-azabicyclo[2.2.2]oct-3-yl)-6-benzo[1,3]dioxol-5-yl-2,3,6,7,12,12a-hexahydropyrazino-[1',2':1,6]pyrido[3,4-b]indole-1,4-dione;

3-((6R,12aR)-6-benzo[1,3]dioxol-5-yl-1,4-dioxo-3,4,6,7,12,12a-hexahydro-1H-pyrazino[1',2':1,6]-pyrido[3,4-b]indol-2-yl)propionic acid ethyl ester;

(6R,12aR)-6-benzo[1,3]dioxol-5-yl-2-(3-methoxypropyl)-2,3,6,7,12,12a-hexahydropyrazino[1',2':1,6]-pyrido[3,4-b]indole-1,4-dione;

N-[2-((6R,12aR)-6-benzo[1,3]dioxol-5-yl-1,4-dioxo-3,4,6,7,12,12a-hexahydro-1H-pyrazino[1',2':1,6]-pyrido[3,4-b]indol-2-yl)-ethyl]-acetamide;

(6R,12aR)-6-benzo[1,3]dioxol-5-yl-2-[3-(2-oxopyrrolidin-1-yl)propyl]-2,3,6,7,12,12a-hexahydropyrazino[1',2':1,6]pyrido[3,4-b]indole-1,4-dione;

2-((6R,12aR)-6-benzo[1,3]dioxol-5-yl-1,4-dioxo-3,4,6,7,12,12a-hexahydro-1H-pyrazino[1',2':1,6]-pyrido[3,4-b]indol-2-yl)-N-phenylacetamide;

(6R,12aR)-6-benzo[1,3]dioxol-5-yl-2-(2-methoxyethyl)-2,3,6,7,12,12a-hexahydropyrazino[1',2':1,6]pyrido[3,4-b]indole-1,4-dione;

2-((6R,12aR)-6-benzo[1,3]dioxol-5-yl-1,4-dioxo-3,4,6,7,12,12a-hexahydro-1H-pyrazino[1',2':1,6]-pyrido[3,4-b]indol-2-yl)-N-benzylacetamide;

(6R,12aR)-6-benzo[1,3]dioxol-5-yl-2-(2-oxo-2-piperidin-1-ylethyl)-2,3,6,7,12,12a-hexahydropyrazino-[1',2':1,6]pyrido[3,4-b]indole-1,4-dione;

(6R,12aR)-6-benzo[1,3]dioxol-5-yl-2-(3-imidazol-1-ylpropyl)-2,3,6,7,12,12a-hexahydropyrazino-[1',2':1,6]pyrido[3,4-b]indole-1,4-dione;

3-((6R,12aR)-6-benzo[1,3]dioxol-5-yl-1,4-dioxo-3,4,6,7,12,12a-hexahydro-1H-pyrazino[1',2':1,6]-pyrido[3,4-b]indol-2-yl)-N-cyclohexylpropionamide;

3-((6R,12aR)-6-benzo[1,3]dioxol-5-yl-1,4-dioxo-3,4,6,7,12,12a-hexahydro-1H-pyrazino[1',2':1,6]-indol-2-yl)-N-butyl-N-methylpropionamide;

4-((6R,12aR)-6-benzo[1,3]dioxol-5-yl-1,4-dioxo-3,4,6,7,12,12a-hexahydro-1H-pyrazino[1',2':1,6]-pyrido[3,4-b]indol-2-yl)-N-cyclohexylbutyramide;

3-((6R,12aS)-6-benzo[1,3]dioxol-5-yl-1,4-dioxo-3,4,6,7,12,12a-hexahydro-1H-pyrazino[1',2':1,6]-pyrido[3,4-b]indol-2-yl)propionic acid;

(+−,cis)-6-benzo[1,3]dioxol-5-yl-2-(tetrahydrofuran-2-ylmethyl)-2,3,6,7,12,12a-hexahydropyrazino[1',2':1,6]pyrido[3,4-b]indole-1,4-dione;

2-((6R,12aR)-6-benzo[1,3]dioxol-5-yl-1,4-dioxo-3,4,6,7,12,12a-hexahydro-1H-pyrazino[1',2':1,6]-pyrido[3,4-b]indol-2-yl)-N-pyridin-4-ylacetamide;

(6R,12aR)-6-benzo[1,3]dioxol-5-yl-2-(3-ethoxypropyl)-2,3,6,7,12,12a-hexahydropyrazino-[1',2':1,6]pyrido[3,4-b]indole-1,4-dione;

(6R,12aR)-6-benzo[1,3]dioxol-5-yl-2-[2-(2-hydroxyethoxy)ethyl]-2,3,6,7,12,12a-hexahydropyrazino-[1',2':1,6]pyrido[3,4-b]indole-1,4-dione;

(6R,12aR)-6-benzo[1,3]dioxol-5-yl-2-((R)-2-hydroxypropyl)-2,3,6,7,12,12a-hexahydropyrazino-[1',2':1,6]pyrido[3,4-b]indole-1,4-dione;

(6R,12aR)-6-benzo[1,3]dioxol-5-yl-2-[2-oxo-2-(4-phenylpiperazin-1-yl)ethyl]-2,3,6,7,12,12a-hexahydropyrazino[1',2':1,6]pyrido[3,4-b]indole-1,4-dione;

2-((6R,12aR)-6-benzo[1,3]dioxol-5-yl-1,4-dioxo-3,4,6,7,12,12a-hexahydro-1H-pyrazino[1',2':1,6]-pyrido[3,4-b]indol-2-yl)-N-methyl-N-phenylacetamide;

(+−,cis)-2-[2-(3-azabicyclo[3.2.2]non-3-yl)-ethyl]-6-benzo[1,3]dioxol-5-yl-2,3,6,7,12,12a-hexahydropyrazino[1',2':1,6]pyrido[3,4-b]indole-1,4-dione;

(6R,12aS)-6-benzo[1,3]dioxol-5-yl-2-(1H-benzoimidazol-2-ylmethyl)-2,3,6,7,12,12a-hexahydropyrazino[1',2':1,6]pyrido[3,4-b]indole-1,4-dione;

(6R,12aR)-6-benzo[1,3]dioxol-5-yl-2-[2-(4-methylpiperazin-1-yl)ethyl]-2,3,6,7,12,12a-hexahydropyrazino[1',2':1,6]pyrido[3,4-b]indole-1,4-dione;

4-((6R,12aR)-6-benzo[1,3]dioxol-5-yl-1,4-dioxo-3,4,6,7,12,12a-1H-pyrazino[1',2':1,6]-pyrido[3,4-b]indole-2-ylmethyl)benzoic acid;

(6R,12aR)-6-benzo[1,3]dioxol-5-yl-2-(4-dimethylaminobenzyl)-2,3,6,7,12,12a-hexahydropyrazino-[1',2':1,6]pyrido[3,4-b]indole-1,4-dione;

(6R,12aR)-6-benzo[1,3]dioxol-5-yl-2-(4-dimethylaminobenzyl)-3-methyl-2,3,6,7,12,12a-hexahydropyrazino[1',2':1,6]pyrido[3,4-b]indole-1,4-dione;

(+−,trans)-6-benzo[1,3]dioxol-5-yl-2-[2-((2R,6S)-2,6-dimethylmorpholin-4-yl)ethyl]-2,3,6,7,12,12a-hexahydropyrazino[1',2':1,6]pyrido[3,4-b]indole-1,4-dione;

(+−,cis)-6-benzo[1,3]dioxol-5-yl-2-[2-((2S,6R)-2,6-dimethylmorpholin-4-yl)ethyl]-2,3,6,7,12,12a-hexahydropyrazino[1',2':1,6]pyrido[3,4-b]indole-1,4-dione;

(6R,12aR)-2-[2-((2S,6R)-2,6-dimethyl-morpholin-4-yl)ethyl]-6-(4-methoxyphenyl)-2,3,6,7,12,12a-hexahydropyrazino[1',2':1,6]pyrido[3,4-b]indole-1,4-dione;
(6R,12aR)-6-benzo[1,3]dioxol-5-yl-2-(2-imidazol-1-ylethyl)-2,3,6,7,12,12a-hexahydropyrazino-[1',2':1,6]pyrido[3,4-b]indole-1,4-dione;
(6R,12aR)-6-benzo[1,3]dioxol-5-yl-2-[2-(2-methylimidazol-1-yl)ethyl]-2,3,6,7,12,12a-hexahydropyrazino[1',21:1,6]pyrido[3,4-b]indole-1,4-dione;
(6R,12aR)-6-benzo[1,3]dioxol-5-yl-2-(2-imidazol-1-ylethyl)-2,3,6,7,12,12a-hexahydropyrazino-[1',2':1,6]pyrido[3,4-b]indole-1,4-dione;
(6R,12aR)-2-(4-aminobenzyl)-6-benzo[1,3]-dioxol-5-yl-2,3,6,7,12,12a-hexahydropyrazino-[1',2':1,6]pyrido[3,4-b]indole-1,4-dione;
N-[4-((6R,12aR)-6-benzo[1,3]dioxol-5-yl-1,4-pyrazino[1',2':1,6]pyrido[3,4-b]indol-2-yl-methyl)phenyl]-1,1,1-trifluoromethanesulfonamide;
4-((6R,12aR)-6-benzo[1,3]dioxol-5-yl-1,4-dioxo-3,4,6,7,12,12a-hexahydro-1H-pyrazino[1',2':1,6]-pyrido[3,4-b]indol-2-ylmethyl)-benzenesulfonamide;
4-((6R,12aR)-6-benzo[1,3]dioxol-5-yl-1,4-dioxo-3,4,6,7,12,12a-hexahydro-1H-pyrazino[1',2':1,6]-pyrido[3,4-b]indol-2-ylmethyl)-benzonitrile;
(6-benzo[1,3]dioxol-4-yl-1,4-dioxo-3,4,6,7,12,12a-hexahydropyrazino[1',2':1,6]pyrido[3,4-b]indol-2-yl)acetonitrile;
(6R,12aR)-6-benzo[1,3]dioxol-5-yl-2-(1H-benzoimidazol-2-ylmethyl)-2,3,6,7,12,12a-hexahydropyrazino[1',2':1,6]pyrido[3,4-b]indole-1,4-dione;
3-((6R,12aR)-6-benzo[1,3]dioxol-5-yl-1,4-dioxo-3,4,6,7,12,12a-hexahydro-1H-pyrazino[1',2':1,6]-pyrido[3,4-b]indol-2-ylmethyl)-benzoic acid methyl ester;
(+−,cis)-6-benzo[1,3]dioxol-5-yl-2-[2-(1-methylpyrrolidin-2-yl)ethyl]-2,3,6,7,12,12a-hexahydropyrazino[1',2':1,6]pyrido[3,4-b]indole-1,4-dione;
(6R,12aR)-6-benzo[1,3]dioxol-5-yl-2-[2-(1H-imidazol-4-yl)ethyl]-2,3,6,7,12,12a-hexahydropyrazino-[1',2':1,6]pyrido[3,4-b]indole-1,4-dione;
(6R,12aR)-6-benzo[1,3]dioxol-5-yl-2-(4-dimethylaminomethylbenzyl)-2,3,6,7,12,12a-hexahydropyrazino[1',2':1,6]pyrido[3,4-b]indole-1,4-dione;
(6R,12aR)-2-[2-(4-aminophenyl)ethyl]-6-benzo[1,3]dioxol-5-yl-2,3,6,7,12,12a-hexahydropyrazino-[1',2':1,6]pyrido[3,4-b]indole-1,4-dione;
((6R,12aR)-6-benzo[1,3]dioxol-5-yl-1,4-dioxo-3,4,6,7,12,12a-hexahydro-1H-pyrazino[1',2':1,6]pyrido-[3,4-b]indol-2-yl)acetic acid benzyl ester;
((6R,12aR)-6-benzo[1,3]dioxol-5-yl-1,4-dioxo-3,4,6,7,12,12a-hexahydro-1H-pyrazino[1',2':1,6]pyrido-[3,4-b]indol-2-yl)acetic acid;
(6R,12aR)-6-benzo[1,3]dioxol-5-yl-2-[3-(3,5-dimethylpyrazol-1-yl)propyl]-2,3,6,7,12,12a-hexahydropyrazino[1',2':1,6]pyrido[3,4-b]indole-1,4-dione;
3-((6R,12aR)-6-benzo[1,3]dioxol-5-yl-1,4-dioxo-3,4,6,7,12,12a-hexahydro-1H-pyrazino[1',2':1,6]-pyrido[3,4-b]indol-2-yl)propionic acid tert-butyl ester;
3-((6R,12aR)-6-benzo[1,3]dioxol-5-yl-1,4-dioxo-3,4,6,7,12,12a-hexahydro-1H-pyrazino[1',2':1,6]-pyrido[3,4-b]indol-2-yl)propionic acid;
(6R,12aR)-6-benzo[1,3]dioxol-5-yl-2-(3-dimethylaminomethylbenzyl)-2,3,6,7,12,12a-hexahydropyrazino[1',2':1,6]pyrido[3,4-b]indole-1,4-dione;
(6R,12aR)-6-benzo[1,3]dioxol-5-yl-2-(2-pyrazol-1-ylethyl)-2,3,6,7,12,12a-hexahydropyrazino-[1',2':1,6]pyrido[3,4-b]indole-1,4-dione;
(6R,12aR)-6-benzo[1,3]dioxol-5-yl-2-(3-nitrobenzyl)-2,3,6,7,12,12a-hexahydropyrazino-[1',2':1,6]pyrido[3,4-b]indole-1,4-dione;
(6R,12aR)-2-(3-aminobenzyl)-6-benzo[1,3]-dioxol-5-yl-2,3,6,7,12,12a-hexahydropyrazino-[1',2':1,6]pyrido[3,4-b]indole-1,4-dione;
N-[3-((6R,12aR)-6-benzo[1,3]dioxol-5-yl-4-dioxo-3,4,6,7,12,12a-hexahydro-1H-pyrazino[1',2':1,6]-pyrido[3,4-b]indole-2-ylmethyl)phenyl]-1,1,1-trifluoromethanesulfonamide;
(6R,12aR)-6-benzofuran-5-yl-2-(2-pyrazol-1-ylethyl)-2,3,6,7,12,12a-hexahydropyrazino[1',2':1,6]-pyrido[3,4-b]indole-1,4-dione;
(6R,12aR)-6-benzo[1,3]dioxol-5-yl-2-(3-pyrazol-1-ylpropyl)-2,3,6,7,12,12a-hexahydropyrazino-[1',2':1,6]pyrido[3,4-b]indole-1,4-dione;
(6R,12aR)-6-benzo[1,3]dioxol-5-yl-2-(4-benzyloxybenzyl)-2,3,6,7,12,12a-hexahydropyrazino-[1',2':1,6]pyrido[3,4-b]indole-1,4-dione;
(6R,12aR)-6-benzo[1,3]dioxol-5-yl-2-[4-(2-dimethylaminoethoxy)benzyl]-2,3,6,7,12,12a-hexahydropyrazino[1,2':1,6]pyrido[3,4-b]indole-1,4-dione;
(6R,12aR)-6-benzo[1,3]dioxol-5-yl-2-(2-[1,4,5]triazol-1-ylethyl)-2,3,6,7,12,12a-hexahydropyrazino[1',2':1,6]pyrido[3,4-b]indole-1,4-dione;
(6R,12aR)-6-benzo[1,3]dioxol-5-yl-2-(4-methylamino-3-nitrobenzyl)-2,3,6,7,12,12a-hexahydropyrazino[1',2':1,6]pyrido[3,4-b]indole-1,4-dione;
2-((6R,12aR)-6-benzo[1,3]dioxol-5-yl-1,4-dioxo-3,4,6,7,12,12a-hexahydro-1H-pyrazino[1',2':1,6]-pyrido[3,4-b]indol-2-yl)-N-(4-methyl-piperazin-1-yl)acetamide;
(6R,12aR)-6-benzo[1,3]dioxol-5-yl-2-(1-methyl-1H-benzoimidazol-5-ylmethyl)-2,3,6,7,12,12a-hexahydropyrazino[1',2':1,6]pyrido[3,4-b]indole-1,4-dione;
((6R,12aR)-6-benzo[1,3]dioxol-5-yl-1,4-dioxo-3,4,6,7,12,12a-hexahydro-1H-pyrazino[1',2':1,6]pyrido-[3,4-b]indol-2-yl)acetic acid tert-butyl ester;
((6R,12aR)-6-benzo[1,3]dioxol-5-yl-1,4-dioxo-3,4,6,7,12,12a-hexahydro-1H-pyrazino[1',2':1,6]pyrido-[3,4-b]indol-2-yl)acetic acid methyl ester;
((6R,12aR)-6-benzo[1,3]dioxol-5-yl-1,4-dioxo-3,4,6,7,12,12a-hexahydro-1H-pyrazino[1',2':1,6]pyrido-[3,4-b]indol-2-yl)acetic acid octyl ester;
and pharmaceutically acceptable salts and solvates thereof.

* * * * *

UNITED STATES PATENT AND TRADEMARK OFFICE
CERTIFICATE OF CORRECTION

PATENT NO. : 6,911,542 B2
DATED : June 28, 2005
INVENTOR(S) : Mark W. Orme et al.

It is certified that error appears in the above-identified patent and that said Letters Patent is hereby corrected as shown below:

Column 1,
Line 49 "C(=O)-C$_{1-4}$alkylenearyl" should be -- C(=O)C$_{1-4}$alkylenearyl --.
Line 50, "C$_{1-4}$-alkylenearyl" should be -- C$_{1-4}$alkylenearyl --.
Line 55, "C$_{1-4}$-alkyleneHet" should be -- C$_{1-4}$alkyleneHet --.
Line 56, "C$_{1-4}$-alkyleneC(=O)C$_{1-4}$alkyleneheteroaryl" should be
-- C$_{1-4}$alkyleneC(=O)C$_{1-4}$alkyleneheteroaryl --.
Line 58, C$_{1-4}$alkyleneC(=O)-NR$^a$R$^{c}$" should be -- C$_{1-4}$alkyleneC(=O)NR$^a$R$^c$ --.
Lines 59-60, "C$_{1-4}$-alkyleneOC$_{1-4}$alkyleneOR$^a$" should be
-- C$_{1-4}$alkyleneOC$_{1-4}$alkyleneOR$^a$ --.
Line 63, "C$_{1-4}$alkyleneOC$_{1-4}$-alkyleneC(=O)OR$^a$" should be
-- C$_{1-4}$alkyleneOC$_{1-4}$alkyleneC(=O)OR$^a$ --.

Column 2,
Line 15, "heteroaryl-C$_{1-3}$alkyl" should be -- heteroarylC$_{1-3}$alkyl --.

Column 3,
Line 60, "C$_{1-4}$-alkyleneOC$_{1-4}$-alkyleneOR$^a$" should be
-- C$_{1-4}$alkyleneOC$_{1-4}$alkyleneOR$^a$ --.

Column 4,
Line 14, "C$_{1-4}$alkyleneC(=O)-NR$^a$R$^{c}$" should be -- C$_{1-4}$alkyleneC(=O)NR$^a$R$^c$ --.

Column 13,
Line 53, "(1R)" should be -- (IR) --.

Column 16,
Line 16, "EXAMPLE 2" should be located beneath the structure, not as a heading to a column.
Line 39, "C$_{20}$H$_{18}$N$_2$O$_4$HCl" should be -- C$_{20}$H$_{18}$N$_2$O$_4$·HCl --.

Column 17,
Lines 3 and 31, "1,6]-pyrido" should be -- 1,6]pyrido --.

Column 18,
Line 14, "1,6]-pyrido" should be -- 1,6]pyrido --.

Column 26,
Line 63, "CGMP" should be -- cGMP --.

UNITED STATES PATENT AND TRADEMARK OFFICE
CERTIFICATE OF CORRECTION

PATENT NO. : 6,911,542 B2
DATED : June 28, 2005
INVENTOR(S) : Mark W. Orme et al.

It is certified that error appears in the above-identified patent and that said Letters Patent is hereby corrected as shown below:

Column 28,
Line 45, "yl--1" should be -- yl-1 --.
Lines 46 and 57, "6]-p" should be -- 6]p --.
Line 65, "+-" should be -- + - --.
Line 66, "zino-[1" should be -- zino[1 --.

Column 29,
Lines 1, 4, 7, 10, 13, 16, 28, 31, 34 and 41, "+-" should be -- + - --.
Lines 2, 5, 11, 14, 17, 20, 26, 28, 35, 39, 42 and 66, "zino-[1" should be -- zino[1 --.
Line 28, "ido-[1" should be -- ido[1 --.
Lines 45, 48, 51, 57, 60 and 63, "6]-pyrido" should be -- 6]pyrido --.

Column 30,
Lines 2, 23, 27, 30 and 54, "zino-[1" should be -- zino[1 --.
Lines 5, 11, 14, 20 and 37, "6]-pyrido" should be -- 6]pyrido --.
Line 8, "6]-indol" should be -- 6]indol --.
Lines 39, 60 and 64, "+-" should be -- + - --.

Column 31,
Lines 6, 13, 16, 40 and 47, "zino-[1" should be -- zino[1 --.
Line 10, "21" should be -- 2' --.
Lines 22, 25, 34 and 60, "6]-pyrido" should be -- 6]pyrido --.
Line 36, "+-" should be -- + - --.
Lines 50 and 53, "pyrido-[3" should be -- pyrido[3 --.

Column 32,
Lines 2, 19, 23 and 43, "6]-pyrido" should be -- 6]pyrido --.
Lines 9, 12, 15, 26 and 29, "zino-[1" should be -- zino[1 --.

UNITED STATES PATENT AND TRADEMARK OFFICE
CERTIFICATE OF CORRECTION

PATENT NO. : 6,911,542 B2
DATED : June 28, 2005
INVENTOR(S) : Mark W. Orme et al.

It is certified that error appears in the above-identified patent and that said Letters Patent is hereby corrected as shown below:

Column 32 (cont'd),
Lines 51, 54 and 57, "pyrido-[3" should be -- pyrido[3 --.

Signed and Sealed this

Twenty-ninth Day of November, 2005

JON W. DUDAS
*Director of the United States Patent and Trademark Office*